US010716662B2

(12) United States Patent
Delaloye et al.

(10) Patent No.: US 10,716,662 B2
(45) Date of Patent: Jul. 21, 2020

(54) STENT-VALVES FOR VALVE REPLACEMENT AND ASSOCIATED METHODS AND SYSTEMS FOR SURGERY

(71) Applicant: Symetis SA, Ecublens (CH)

(72) Inventors: Stephane Delaloye, Bulach (CH); Jean-Luc Hefti, Cheseaux-Noreaz (CH); Serge Delaloye, Chamoson (CH)

(73) Assignee: Boston Scientific Limited, Hamilton (BM)

( * ) Notice: Subject to any disclaimer, the term of this patent is extended or adjusted under 35 U.S.C. 154(b) by 0 days.

(21) Appl. No.: 13/861,782

(22) Filed: Apr. 12, 2013

(65) Prior Publication Data

US 2014/0039614 A1    Feb. 6, 2014

Related U.S. Application Data

(63) Continuation of application No. 13/598,918, filed on Aug. 30, 2012, now abandoned, which is a continuation of application No. 13/351,438, filed on Jan. 17, 2012, now abandoned, which is a continuation of application No. 13/150,723, filed on Jun. 1, 2011, now abandoned, which is a continuation of application No. 12/674,112, filed as application
(Continued)

(51) Int. Cl.
*A61F 2/24* (2006.01)
(52) U.S. Cl.
CPC ............ *A61F 2/2418* (2013.01); *A61F 2/243* (2013.01); *A61F 2/2436* (2013.01); *A61F 2220/0075* (2013.01); *A61F 2250/0018* (2013.01)

(58) Field of Classification Search
CPC ........ A61F 2/24; A61F 2/2418; A61F 2/2412; A61F 2/243; A61F 2/2436; A61F 2220/0075; A61F 2250/0018
USPC ........... 623/2.1, 2.12, 2.14, 2.17, 2.18, 2.36, 623/2.38, 1.15, 1.24, 1.26, 1.36, 1.37
See application file for complete search history.

(56) References Cited

U.S. PATENT DOCUMENTS 3,755,823 A * 9/1973 Hancock ............... A61F 2/2418
623/2.18
3,781,969 A    1/1974 Anderson
(Continued)

FOREIGN PATENT DOCUMENTS

AU    2006328896 A1    6/2007
AU    2007294199 A1    3/2008
(Continued)

OTHER PUBLICATIONS

Liu et al. Effect of Fiber Orientation on the Stress Distribution within a Leaflet of a Polymer Composite Heart Valve in the Closed Position. Journal of Biomechanics. 2007 (40): 1099-1106.*
(Continued)

*Primary Examiner* — Suba Ganesan
(74) *Attorney, Agent, or Firm* — Seager, Tufte & Wickhelm LLP

(57) ABSTRACT

A stent-valve having a valve component and a stent component for housing the valve component, as well as associated methods and systems for delivery of the stent-valve via minimally-invasive surgery. The stent-valve can be configurable between two or more configurations to assist in delivery of the stent-valve to an implantation site of a patient.

20 Claims, 14 Drawing Sheets

Related U.S. Application Data

No. PCT/IB2008/002180 on Aug. 21, 2008, now abandoned.

(60) Provisional application No. 60/965,780, filed on Aug. 21, 2007.

(56) References Cited

U.S. PATENT DOCUMENTS

| | | | |
|---|---|---|---|
| 4,106,129 A * | 8/1978 | Carpentier et al. | 623/2.18 |
| 4,191,218 A * | 3/1980 | Clark | A61F 2/06 |
| | | | 139/383 R |
| 4,470,157 A | 9/1984 | Love | |
| 4,477,930 A | 10/1984 | Totten et al. | |
| 4,834,755 A | 5/1989 | Silvestrini et al. | |
| 5,078,720 A | 1/1992 | Burton et al. | |
| 5,163,955 A | 11/1992 | Love et al. | |
| 5,192,301 A | 3/1993 | Kamiya et al. | |
| 5,344,442 A | 9/1994 | Deac | |
| 5,354,330 A | 10/1994 | Hanson | |
| 5,411,552 A | 5/1995 | Andersen et al. | |
| 5,480,424 A | 1/1996 | Cox | |
| 5,499,995 A | 3/1996 | Teirstein et al. | |
| 5,500,015 A | 3/1996 | Deac | |
| 5,540,712 A | 7/1996 | Kleshinski et al. | |
| 5,571,174 A | 11/1996 | Love et al. | |
| 5,609,626 A | 3/1997 | Quijano | |
| 5,653,749 A | 8/1997 | Love et al. | |
| 5,662,703 A | 9/1997 | Yurek et al. | |
| 5,693,085 A | 12/1997 | Buirge et al. | |
| 5,713,950 A | 2/1998 | Cox | |
| 5,713,951 A | 2/1998 | Garrison et al. | |
| 5,718,725 A | 2/1998 | Sterman | |
| 5,769,882 A | 6/1998 | Fogarty et al. | |
| 5,797,960 A | 8/1998 | Stevens | |
| 5,807,327 A | 9/1998 | Green et al. | |
| 5,817,126 A | 10/1998 | Imran | |
| 5,823,956 A | 10/1998 | Roth | |
| 5,824,041 A | 10/1998 | Lenker et al. | |
| 5,840,081 A | 11/1998 | Andersen et al. | |
| 5,843,158 A | 12/1998 | Lenker et al. | |
| 5,855,600 A | 1/1999 | Alt | |
| 5,855,601 A | 1/1999 | Bessler et al. | |
| 5,861,028 A | 1/1999 | Angell | |
| 5,924,424 A | 7/1999 | Stevens et al. | |
| 5,938,697 A | 8/1999 | Killion et al. | |
| 5,957,949 A | 9/1999 | Leonhardt et al. | |
| 5,957,974 A | 9/1999 | Thompson et al. | |
| 5,976,174 A | 11/1999 | Ruiz | |
| 5,980,533 A | 11/1999 | Holman | |
| 6,029,671 A | 2/2000 | Stevens | |
| 6,083,257 A | 7/2000 | Taylor et al. | |
| 6,102,944 A | 8/2000 | Huynh et al. | |
| 6,110,201 A | 8/2000 | Quijano | |
| 6,168,614 B1 | 1/2001 | Andersen et al. | |
| 6,171,335 B1 | 1/2001 | Wheatley | |
| 6,183,481 B1 | 2/2001 | Lee et al. | |
| 6,196,230 B1 | 3/2001 | Hall et al. | |
| 6,214,036 B1 | 4/2001 | Letendre et al. | |
| 6,254,564 B1 | 7/2001 | Wilk | |
| 6,287,334 B1 | 9/2001 | Moll et al. | |
| 6,287,339 B1 | 9/2001 | Vazquez et al. | |
| 6,331,189 B1 | 12/2001 | Wolinsky et al. | |
| 6,350,278 B1 | 2/2002 | Lenker et al. | |
| 6,364,905 B1 * | 4/2002 | Simpson | A61F 2/2412 |
| | | | 623/2.13 |
| 6,379,383 B1 | 4/2002 | Palmaz et al. | |
| 6,401,720 B1 | 6/2002 | Stevens et al. | |
| 6,406,493 B1 | 6/2002 | Quijano | |
| 6,409,759 B1 | 6/2002 | Peredo | |
| 6,454,799 B1 | 9/2002 | Schreck | |
| 6,458,153 B1 | 10/2002 | Bailey | |
| 6,530,952 B2 | 3/2003 | Vesely | |
| 6,533,807 B2 | 3/2003 | Wolinsky et al. | |
| 6,537,310 B1 | 3/2003 | Palmaz | |
| 6,569,196 B1 | 3/2003 | Vesely | |
| 6,562,069 B2 | 5/2003 | Cai et al. | |
| 6,572,652 B2 | 6/2003 | Shaknovich | |
| 6,582,462 B1 | 6/2003 | Andersen et al. | |
| 6,589,279 B1 | 7/2003 | Anderson | |
| 6,613,079 B1 | 9/2003 | Wolinsky et al. | |
| 6,635,085 B1 | 10/2003 | Caffey et al. | |
| 6,652,555 B1 | 11/2003 | Van Tassel et al. | |
| 6,682,558 B2 | 1/2004 | Tu | |
| 6,682,559 B2 | 1/2004 | Myers | |
| 6,695,865 B2 | 2/2004 | Boyle | |
| 6,719,787 B2 | 4/2004 | Cox | |
| 6,730,118 B2 | 5/2004 | Spenser et al. | |
| 6,733,525 B2 | 5/2004 | Yang | |
| 6,736,827 B1 | 5/2004 | McAndrew | |
| 6,755,855 B2 | 6/2004 | Yurek et al. | |
| 6,767,362 B2 | 7/2004 | Schreck | |
| 6,790,229 B1 | 9/2004 | Berreklouw | |
| 6,805,711 B2 | 10/2004 | Quijano | |
| 6,830,584 B1 | 12/2004 | Seguin | |
| 6,830,585 B1 | 12/2004 | Artof | |
| 6,830,586 B2 | 12/2004 | Quijano | |
| 6,849,085 B2 | 2/2005 | Marton | |
| 6,875,231 B2 | 4/2005 | Anduiza et al. | |
| 6,893,460 B2 | 5/2005 | Spenser et al. | |
| 6,908,481 B2 | 6/2005 | Cribier | |
| 6,936,066 B2 | 8/2005 | Palmaz | |
| 6,942,682 B2 | 9/2005 | Vrba et al. | |
| 7,018,406 B2 | 3/2006 | Seguin et al. | |
| 7,025,773 B2 | 4/2006 | Gittings et al. | |
| 7,025,780 B2 | 4/2006 | Gabbay | |
| 7,041,132 B2 | 5/2006 | Quijano et al. | |
| 7,044,966 B2 | 5/2006 | Svanidze | |
| 7,101,396 B2 | 9/2006 | Artof et al. | |
| 7,141,064 B2 | 11/2006 | Scott | |
| 7,179,290 B2 | 2/2007 | Cao | |
| 7,195,641 B2 | 3/2007 | Palmaz | |
| 7,198,646 B2 | 4/2007 | Figulla et al. | |
| 7,201,772 B2 | 4/2007 | Schwammenthal et al. | |
| 7,217,287 B2 | 5/2007 | Wilson | |
| 7,252,682 B2 | 8/2007 | Seguin | |
| 7,276,078 B2 | 10/2007 | Spenser | |
| 7,285,130 B2 | 10/2007 | Austin | |
| 7,316,712 B2 | 1/2008 | Peredo | |
| 7,318,278 B2 | 1/2008 | Zhang | |
| 7,320,704 B2 | 1/2008 | Lashinski et al. | |
| 7,320,705 B2 | 1/2008 | Quintessenza | |
| 7,329,278 B2 | 2/2008 | Seguin et al. | |
| 7,329,279 B2 | 2/2008 | Haug et al. | |
| 7,331,991 B2 | 2/2008 | Kheradvar | |
| 7,331,993 B2 | 2/2008 | White | |
| 7,338,484 B2 | 3/2008 | Schoon | |
| 7,361,189 B2 | 4/2008 | Case | |
| 7,371,258 B2 | 5/2008 | Woo | |
| 7,374,571 B2 | 5/2008 | Pease | |
| 7,377,938 B2 | 5/2008 | Sarac et al. | |
| 7,381,218 B2 | 6/2008 | Schreck | |
| 7,381,219 B2 | 6/2008 | Salahieh et al. | |
| 7,393,358 B2 | 7/2008 | Malewicz | |
| 7,393,360 B2 | 7/2008 | Spenser et al. | |
| 7,399,315 B2 | 7/2008 | Iobbi | |
| 7,402,171 B2 | 7/2008 | Osborne | |
| 7,410,499 B2 | 8/2008 | Bicer | |
| 7,416,530 B2 | 8/2008 | Turner | |
| 7,422,603 B2 | 9/2008 | Lane | |
| 7,431,733 B2 | 10/2008 | Knight | |
| 7,435,257 B2 | 10/2008 | Lashinski | |
| 7,445,632 B2 | 11/2008 | McGuckin, Jr. et al. | |
| 7,455,689 B2 | 11/2008 | Johnson | |
| 7,470,284 B2 | 12/2008 | Lambrecht | |
| 7,470,285 B2 | 12/2008 | Nugent et al. | |
| 7,473,275 B2 | 1/2009 | Marquez | |
| 7,500,989 B2 | 3/2009 | Solem | |
| 7,503,929 B2 | 3/2009 | Johnson | |
| 7,503,930 B2 | 3/2009 | Sharkawy | |
| 7,510,572 B2 | 3/2009 | Gabbay | |
| 7,510,575 B2 | 3/2009 | Spenser et al. | |
| 7,513,909 B2 | 4/2009 | Lane | |
| 7,534,261 B2 | 5/2009 | Friedman | |

(56) References Cited

U.S. PATENT DOCUMENTS

| | | |
|---|---|---|
| 7,556,646 B2 | 7/2009 | Yang et al. |
| 7,578,828 B2 | 8/2009 | Gittings et al. |
| 7,585,321 B2 | 9/2009 | Cribier |
| 7,591,848 B2 | 9/2009 | Allen |
| 7,618,446 B2 | 11/2009 | Andersen et al. |
| 7,481,838 B2 | 12/2009 | Carpentier |
| 7,625,403 B2 | 12/2009 | Krivoruchko |
| 7,632,296 B2 | 12/2009 | Malewicz |
| 7,682,390 B2 | 3/2010 | Seguin |
| 7,780,726 B2 | 8/2010 | Seguin |
| 7,846,203 B2 | 12/2010 | Cribier |
| 7,846,204 B2 | 12/2010 | Letac et al. |
| 7,896,915 B2 | 3/2011 | Guyenot et al. |
| 7,914,575 B2 | 3/2011 | Guyenot et al. |
| 7,947,075 B2 | 5/2011 | Goetz et al. |
| 7,959,672 B2 | 6/2011 | Salahieh et al. |
| 8,002,825 B2 | 8/2011 | Letac et al. |
| 8,052,749 B2 | 11/2011 | Salahieh |
| 8,057,540 B2 | 11/2011 | Letac et al. |
| 8,092,518 B2 | 1/2012 | Schreck |
| 8,092,520 B2 | 1/2012 | Quadri |
| 8,603,159 B2 | 12/2013 | Seguin |
| 8,628,571 B1 | 1/2014 | Hacohen |
| 8,845,721 B2 | 9/2014 | Braido et al. |
| 2001/0007956 A1 | 7/2001 | Letac et al. |
| 2001/0011187 A1 | 8/2001 | Pavcnik et al. |
| 2002/0177894 A1 | 11/2002 | Acosta et al. |
| 2003/0023300 A1 | 1/2003 | Bailey et al. |
| 2003/0028213 A1 | 2/2003 | Thill |
| 2003/0040792 A1 | 2/2003 | Gabbay |
| 2003/0042186 A1* | 3/2003 | Boyle .................. 210/136 |
| 2003/0109924 A1 | 6/2003 | Cribier |
| 2003/0114913 A1 | 6/2003 | Spenser et al. |
| 2004/0019374 A1 | 1/2004 | Hojeibane et al. |
| 2004/0044361 A1 | 1/2004 | Atsumi |
| 2004/0044400 A1 | 3/2004 | Cheng et al. |
| 2004/0082989 A1 | 4/2004 | Cook et al. |
| 2004/0093063 A1 | 5/2004 | Wright |
| 2004/0106976 A1 | 6/2004 | Bailey et al. |
| 2004/0186563 A1 | 9/2004 | Lobbi |
| 2004/0186565 A1 | 9/2004 | Schreck |
| 2004/0210304 A1 | 10/2004 | Seguin et al. |
| 2004/0254594 A1 | 12/2004 | Alfaro |
| 2004/0260389 A1 | 12/2004 | Case et al. |
| 2005/0043759 A1 | 2/2005 | Chanduszko |
| 2005/0043790 A1 | 2/2005 | Seguin |
| 2005/0070794 A1 | 3/2005 | Deal et al. |
| 2005/0075731 A1* | 4/2005 | Artof et al. ................ 623/2.18 |
| 2005/0113910 A1 | 5/2005 | Paniagua et al. |
| 2005/0137681 A1* | 6/2005 | Shoemaker ........... A61F 2/2418 623/1.23 |
| 2005/0137688 A1 | 6/2005 | Salahieh et al. |
| 2005/0137696 A1 | 6/2005 | Salahieh et al. |
| 2005/0137702 A1 | 6/2005 | Haug et al. |
| 2005/0154446 A1 | 7/2005 | Phillips et al. |
| 2005/0182483 A1 | 8/2005 | Osborne |
| 2005/0240262 A1* | 10/2005 | White ................... A61F 2/2412 623/2.12 |
| 2005/0267523 A1 | 12/2005 | Devellian et al. |
| 2005/0283231 A1 | 12/2005 | Haug et al. |
| 2005/0288706 A1 | 12/2005 | Widomski et al. |
| 2006/0004442 A1* | 1/2006 | Spenser ............... A61F 2/2409 623/2.11 |
| 2006/0122692 A1 | 6/2006 | Gilad et al. |
| 2006/0149360 A1 | 7/2006 | Schwammenthal et al. |
| 2006/0161248 A1 | 7/2006 | Case |
| 2006/0195180 A1 | 8/2006 | Kheradvar et al. |
| 2006/0259136 A1* | 11/2006 | Nguyen et al. ............. 623/2.18 |
| 2006/0259137 A1 | 11/2006 | Artof |
| 2006/0265056 A1 | 11/2006 | Nguyen et al. |
| 2006/0270958 A1* | 11/2006 | George .................... 602/28 |
| 2006/0271166 A1 | 11/2006 | Thill et al. |
| 2006/0287717 A1 | 12/2006 | Rowe |
| 2007/0016283 A1 | 1/2007 | Greenhalgh et al. |
| 2007/0060998 A1 | 3/2007 | Butterwick et al. |
| 2007/0061002 A1 | 3/2007 | Paul, Jr. et al. |
| 2007/0118210 A1 | 5/2007 | Pinchuk |
| 2007/0198097 A1 | 8/2007 | Zegdi |
| 2007/0213813 A1 | 9/2007 | Von Segesser |
| 2007/0225801 A1* | 9/2007 | Drews ................. A61F 2/2412 623/2.11 |
| 2007/0239265 A1 | 10/2007 | Birdsall |
| 2007/0239269 A1 | 10/2007 | Dolan |
| 2007/0244546 A1 | 10/2007 | Francis |
| 2007/0282436 A1 | 12/2007 | Pinchuk |
| 2008/0125859 A1 | 2/2008 | Salahieh |
| 2008/0071361 A1 | 3/2008 | Tuval |
| 2008/0071362 A1 | 3/2008 | Tuval |
| 2008/0071366 A1 | 3/2008 | Tuval |
| 2008/0071368 A1 | 3/2008 | Tuval et al. |
| 2008/0077234 A1 | 3/2008 | Styre |
| 2008/0140189 A1 | 6/2008 | Nguyen |
| 2008/0161909 A1 | 7/2008 | Kheradvar |
| 2008/0177381 A1 | 7/2008 | Navia |
| 2008/0195199 A1 | 8/2008 | Kheradvar |
| 2008/0208327 A1 | 8/2008 | Rowe |
| 2008/0228263 A1 | 9/2008 | Ryan |
| 2008/0234814 A1 | 9/2008 | Salahieh |
| 2008/0255660 A1 | 10/2008 | Guyenot et al. |
| 2008/0269878 A1 | 10/2008 | Iobbi |
| 2008/0275549 A1* | 11/2008 | Rowe ................... A61F 2/2418 623/2.11 |
| 2008/0275550 A1 | 11/2008 | Kheradvar |
| 2009/0005863 A1 | 1/2009 | Goetz et al. |
| 2009/0164006 A1 | 6/2009 | Seguin et al. |
| 2009/0171432 A1 | 7/2009 | Von Segesser et al. |
| 2009/0171447 A1 | 7/2009 | Von Segesser et al. |
| 2009/0276040 A1 | 11/2009 | Rowe et al. |
| 2009/0287299 A1 | 11/2009 | Tabor et al. |
| 2010/0168839 A1 | 7/2010 | Braido et al. |
| 2011/0022157 A1 | 1/2011 | Essinger et al. |
| 2011/0040374 A1 | 2/2011 | Goetz et al. |
| 2011/0224780 A1 | 9/2011 | Tabor et al. |
| 2012/0101571 A1 | 4/2012 | Thambar et al. |
| 2012/0101572 A1 | 4/2012 | Kovalsky et al. |
| 2012/0116496 A1 | 5/2012 | Chuter et al. |
| 2012/0123529 A1 | 5/2012 | Levi et al. |
| 2012/0172982 A1 | 7/2012 | Stacchino et al. |
| 2012/0303116 A1 | 11/2012 | Gorman, III |

FOREIGN PATENT DOCUMENTS

| | | |
|---|---|---|
| AU | 2009200985 A1 | 4/2009 |
| CA | 2634358 A1 | 6/2007 |
| CA | 2657839 A1 | 3/2008 |
| CA | 2659690 A1 | 3/2008 |
| DE | 20003874 U1 | 5/2000 |
| DE | 19857887 A1 | 7/2000 |
| DE | 102005003632 A1 | 8/2006 |
| DE | 202007005491 U1 | 6/2007 |
| DE | 202007005491 U1 | 7/2007 |
| EP | 0328401 A1 | 8/1989 |
| EP | 0 592 410 A1 | 4/1994 |
| EP | 0 657 147 A2 | 6/1995 |
| EP | 0 696 447 A2 | 2/1996 |
| EP | 0 943 302 A2 | 9/1999 |
| EP | 1 093 771 A2 | 4/2001 |
| EP | 1 251 797 A1 | 10/2002 |
| EP | 1 264 582 A2 | 12/2002 |
| EP | 1262201 A1 | 12/2002 |
| EP | 1 267 753 A2 | 1/2003 |
| EP | 1598031 A1 | 11/2005 |
| EP | 1598031 A2 | 11/2005 |
| EP | 1968491 A2 | 9/2008 |
| EP | 2033593 A1 | 3/2009 |
| EP | 2047824 A1 | 4/2009 |
| EP | 2059192 A1 | 5/2009 |
| EP | 2074964 A1 | 7/2009 |
| EP | 2949292 A1 | 12/2015 |
| EP | 2949292 B1 | 5/2016 |
| FR | 2874812 A1 | 3/2006 |
| WO | WO-1998029057 A1 | 7/1998 |
| WO | WO-2000028922 A1 | 5/2000 |
| WO | WO-2000047139 A1 | 8/2000 |

(56) References Cited

FOREIGN PATENT DOCUMENTS

| WO | WO-2000053122 A1 | 9/2000 |
|---|---|---|
| WO | WO-2001049213 A2 | 7/2001 |
| WO | WO-2001062189 A1 | 8/2001 |
| WO | WO-2002067782 A2 | 9/2002 |
| WO | WO-2002076349 A1 | 10/2002 |
| WO | 2003007795 A2 | 1/2003 |
| WO | WO-2003003949 A2 | 1/2003 |
| WO | WO-2003047468 A1 | 6/2003 |
| WO | WO-2003063729 A2 | 8/2003 |
| WO | 03092554 A1 | 11/2003 |
| WO | WO-2005070343 A1 | 8/2005 |
| WO | WO-2005102015 A2 | 11/2005 |
| WO | 2006058163 A2 | 6/2006 |
| WO | WO-2006068944 A2 | 6/2006 |
| WO | WO-2006076890 A1 | 7/2006 |
| WO | WO-2006/083763 A1 | 8/2006 |
| WO | WO-2006086135 A2 | 8/2006 |
| WO | 2006093795 A1 | 9/2006 |
| WO | 2006124649 | 11/2006 |
| WO | 2006127765 A | 11/2006 |
| WO | WO-2006127765 A1 | 11/2006 |
| WO | 2007071436 A2 | 6/2007 |
| WO | 2006086736 A2 | 8/2007 |
| WO | 2007071436 A3 | 11/2007 |
| WO | 2008028569 A1 | 3/2008 |
| WO | 2008040555 A2 | 4/2008 |
| WO | 2008070442 A1 | 6/2008 |
| WO | 2009024859 A2 | 2/2009 |
| WO | 2009053497 A1 | 4/2009 |
| WO | WO-2009024859 A3 | 5/2009 |
| WO | 2009091509 A1 | 7/2009 |
| WO | 2010045297 A2 | 4/2010 |
| WO | 2010049160 A1 | 5/2010 |
| WO | 2010083558 A1 | 7/2010 |
| WO | 2010045238 A2 | 10/2010 |
| WO | 2011051043 A1 | 5/2011 |
| WO | 2011057087 A1 | 5/2011 |
| WO | 2013033791 A1 | 3/2013 |
| WO | 2013134214 A1 | 9/2013 |
| WO | 2014072439 A9 | 7/2014 |

OTHER PUBLICATIONS

Mack, M.J., "Minimally invasive cardiac surgery", Surg Endosc, (2006) 20:S488-S492.
Walther et al., "Transapical approach for sutureless stent-fixed aortic valve implantation: experimental results", European Journal of Cardiao-thoriacic Surgery, 29 (2006), 703-708.
Dewey et al., "Transapical aortic valve implantation: an animal feasability study", The annals of thoracic surgery, (2006):82:110-116.
Akins, et al., "Risk of Preoperative Valve Replacement for Failed Mitral and Aortic Biprothesese", Ann Thorac Surg (1998), 65:1545-52.
Ma,et al., "Double-crowned valved stents for off-pump mitral valvle replacement", European Journal of Cardio-Thoracic Surgery (2005), 28-194-199.
Weerasinghe, et al., "First Redo Heart Valve Replacement: A 10-Year Analysis", Circulation (1999), 99:655-658.
International Search Report for International Application No. PCT/EP2008/064558, date of completion of report, Mar. 18, 2009 and Written Opinion of the International Searching Authority for International Application No. PCT/EP2008/064558.
Communication from the European Examining Division dated Mar. 28, 2014 for corresponding European Patent Application No. 08806901.8.
Pawelec-Wojtalk, "Closure of Left Ventricle Perforation with the Use of Muscular VSD Occluder", European Journal of Cardio-Thoracic Surgery (2005), 27:714-716.
Examination Report, Application No. EP06841127.1, dated Feb. 6, 2009.
European Search Report, EP09154935.2, dated May 29, 2009.
Australian Examination Report, Application No. AU 2009200985, dated Mar. 4, 2010.
European Examination Report, Application No. EP07818037.9, dated Aug. 11, 2009.
International Preliminary Report, Application No. PCT/EP2006/012455, dated Jun. 24, 2008.
International Search Report for PCT/EP2006/012455, dated Sep. 27, 2007.
International Preliminary Report on Patentability, Application No. PCT/EP2007/07413, dated Mar. 10, 2009.
Partial International Search Report for International Application No. PCT/EP2014/055044, filed Mar. 13, 2014.
ISR & WO for PCT/162008/002180, mailed Apr. 15, 2009.
IPRP for PCT/IB2008/002180, issued Feb. 24, 2010.
ISR for PCT/EP2010/057798, mailed Sep. 12, 2010.
IPRP for PCT/EP2010/057798, mailed Dec. 6, 2011.
ISR for PCT/EP2007/007413, mailed Jan. 28, 2008.
IPRP for PCT/EP2007/007413, issued Mar. 10, 2009.
IPRP issued May 8, 2012 for PCT/EP2010/063306.
ISR mailed Feb. 17, 2012 for PCT/EP2011/066677.
IPRP issued Mar. 26, 2013 for PCT/EP2011/066677.
ISR mailed Apr. 17, 2014 for PCT/EP2013/073318.
Ratner, et al., Biomaterials in Science, An Introduction to Materials in Medicine, 1996 (excerpt).
Frenot, et al., Polymer nanofibers assembled by electrospinning, Current Opinion in Colloid and Interface Sci., 8, 64-75, 2003.
Gupta, Medical Textile Structures: An Overview, MDDI Medical Device and Diagnostic Industry News Products and Suppliers, Medical Plastics and Biomaterials Magazine, 1-10, 1998.
Lawler et al., Textiles Technology, Edexcel, Heinemann Educational Publishers, 2002.
McGrath, et al., Early-Phase Events with the Mitroflow Pericardial Valve, Texas Heart Institute Journal, 15, 148-151, 1988.
Mirjalili, et al., Review for application of electrospinning and electrospun nanofibers technology in textile industry, Journal Nanostruct Chem, 6, 207-213, 2016.
Moazami, et al., Transluminal Aortic Vale Placement, A Feasibility Study With a Newly Designed Collapsible Aortic Valve, ASAIO Journal, 42, M381-M385, 1996.
Operath, Lotus Illustrated Dictionary of Textile, 2006.
Rivers, et al., JoAnn Your Guide to Creativity, 322, Sep. 4, 2014.
SewBasic, 34 Essential Skills for Sewing with Confidence, 2002.
Stecker, The Fashion Design Manual, 1996.
Theron et al., Electrostatic field-assisted alignment of electrospun nanofibres, Nanotechnology, Institute of Physics Publishing, 12, 384-390, 2001.
Tsai, et al., Investigation of the Fiber, Bulk, and Surface Properties of Meltblown and Electrospun Polymeric Fabrics, INJ Fall 2004.
Vidyasagar, Textile Spinning and Weaving Technology, Encyclopaedia of Textiles, Mittal Publications, New Delhi, 2000.
Wilson, et al., A Self-Expanding Bifurcated Endovascular Graft for Abdominal Aortic Aneurysm Repair, An Initial Study in a Canine Model, 42(5), M386-M393, 1996.
Vinzenzi-Hombach, Interventionelle Kardiologie, Angiologie und Kardiovaskularchirurgie, Technik, Klink, Therapie, Schattauer, pp. 1-687, 2001.

* cited by examiner

102

202, 204

Flared end of skirt — Component 1, Component 2, Component 3

1204 "bullet" shaped, short tip with coiled reinforced outer stent sheath

1202 "dilator" shaped, long tip with unreinforced outer stent sheath

Gap between proximal and distal component

Gap between proximal and distal component removed

Stentholder proximal of chamfered tip

Stentholder within hollow tip

Chamfered tip

Hollow tip

Stentvalve partially released

Delivery system closed

Stentvalve released

Shaft with bending stiffness gradient 2104 tubing
2102 suture
2106 stentholder with pins

2108 attachment elements constrained by outer sheath

STENT-VALVES FOR VALVE REPLACEMENT AND ASSOCIATED METHODS AND SYSTEMS FOR SURGERY

RELATED APPLICATIONS

This application is a continuation of U.S. patent application Ser. No. 13/598,918, filed Aug. 30, 2012, which is a continuation of U.S. patent application Ser. No. 13/351,438, filed Jan. 17, 2012, which is a continuation of U.S. patent application Ser. No. 13/150,723, filed Jun. 1, 2011, which is a continuation of U.S. patent application Ser. No. 12/674,112, filed Feb. 18, 2010, which is a national stage filing of PG171E2008/002180, filed Aug. 21, 2008, which claims the benefit of priority to U.S. Provisional Application No. 60/965,780, filed Aug. 21, 2007, the entire contents of which are hereby incorporated by reference in their entireties.

BACKGROUND OF THE INVENTION

Conventional approaches for cardiac valve replacement require the cutting of a relatively large opening in the patient's sternum ("sternotomy") or thoracic cavity ("thoracotomy") in order to allow the surgeon to access the patient's heart. Additionally, these approaches require arrest of the patient's heart and a cardiopulmonary bypass (i.e., use of a heart-lung bypass machine to oxygenate and circulate the patient's blood). Despite their invasiveness, these surgical approaches may be reasonably safe for a first intervention. However, tissue adherences resulting from the first surgery may increase the risks (e.g., death) associated with subsequent valve replacement surgeries. See Akins et al., "Risk of Reoperative Valve Replacement for Failed Mitral and Aortic Bioprostheses", Ann Thorac Surg 1998; 65:1545-52; and Weerasinghe et al., "First Redo Heart Valve Replacement—A 10-Year Analysis", Circulation 1999; 99:655-658; each of which is incorporated by reference herein in its entirety.

Synthetic valves and biological valves have been used for cardiac valve replacement with varying results. Synthetic valves rarely fail but require life-long anti-coagulant treatment to prevent blood from clotting (thrombosis) in and around the replacement valve. Such anti-coagulant treatment significantly limits patients' activities and can cause various other complications. Biological valves do not require such anti-coagulation treatment but typically fail within 10-15 years. Thus, to limit the need for and risks associated with re-operation on failed biological valves, traditionally only patients with less than about 10-15 years to live have received biological valve replacements. Patients with longer life expectancies have received synthetic valves and anti-coagulant treatment.

Attempts have been made to develop less-invasive surgical methods for cardiac valve replacement. These surgical methods, referred to as percutaneous heart valve replacement therapies (PHVT), use a catheter to deliver a replacement valve to an implantation site using the patient's vascular system. These PHVT attempts have various shortcomings, including their inability to ensure proper positioning and stability of the replacement valve within the patient's body.

In view of the foregoing, it would be desirable to provide improved methods, systems, and devices for cardiac valve replacement.

SUMMARY OF THE INVENTION

Some embodiments of the present invention are directed to systems, methods, and devices for cardiac valve replacement. For example, these methods, systems, and devices may be applicable to the full range of cardiac-valve therapies including the replacement of failed aortic, mitral, tricuspid, and pulmonary valves. In some embodiments, the present invention may facilitate a surgical approach whereby surgery is performed on a beating heart without the need for an open-chest cavity and heart-lung bypass. This minimally-invasive surgical approach may to reduce the risks associated with replacing a failed native valve in the first instance, as well as the risks associated with secondary or subsequent surgeries to replace failed artificial (e.g., biological or synthetic) valves. Stent-valves according to some embodiments of the present invention may include a valve component and at least one stent component (e.g., a single-stent-valve or a double-stent-valve). The valve component may include a biological or synthetic (e.g., is mechanical) valve and/or any other suitable material(s). The stent and valve components may be capable of at least two configurations: a collapsed configuration (e.g., during delivery) and an expanded configuration (e.g., after implantation).

In some embodiments, the stent component of a stent-valve may include a first strut and a second strut with ends located at different positions along a longitudinal axis of the stent component, wherein the first strut and the second strut provide an axial resistance for anchoring the stent at an implantation site. Multiple installations of the first strut and the second strut may be provided, where such installations are positioned horizontally along a perimeter of the stent component. In some embodiments, the first strut and the second strut may be connected.

Alternatively or additionally, the stent-component of a stent valve may include multiple locking elements protruding outwardly from an outer surface of the stent component, where each locking element includes a first end adjacent to the outer surface of the stent component and a second end spaced apart from the outer surface of the stent component. The second end of at least a first locking element may be located at a different position along a longitudinal axis of the stent component than the second end of at least a second locking element. For example, in one embodiment, the first locking element and the second locking element may have substantially the same lengths, and the first ends of the first and second locking elements may be positioned at multiple, different levels along the longitudinal axis or the stent component. In another embodiment, the first locking element and the second locking element may have different lengths, and the first ends of the first and second locking elements may be positioned at substantially the same level along the longitudinal axis of the stent component.

In some embodiments, the stent component of a stent-valve may include at least a first commissural post and a second commissural post adjacent to a body of the stent component, where the external contours of the first and second commissural posts collectively form a generally concave shape. In some embodiments, each of the external contours may slope inwardly toward the center of the corresponding commissural post in the direction of the body of to the stent component. In other embodiments, external contours of adjacent commissural posts may be generally convexly shaped.

In some embodiments, the valve component of a stent-valve may include an outer surface covered with fabric (e.g., at least a portion thereof, or substantially the entire surface). The valve component may include at least one suture along a free edge of the valve component and at least one suture along an inflow free edge of the valve component, where the fabric includes a skirt that extends below the valve component. A free edge of the skirt may be folded over a bottom portion of the corresponding stent component and sutured to the stent component. In some embodiments, substantially all or at least a portion of the fibers of the fabric are oriented +/−45 degrees with respect to a longitudinal axis of the valve component. Alternatively or additionally, the stent component may include at least one Y-shaped structure fixed to the valve component by one or more (e.g., 3) sutures forming a corresponding Y-shaped configuration. In some embodiments, the stent component comprises an annular groove and the free edge of the skirt is positioned within the groove. Alternatively or additionally, the free edge of the skirt comprises at least one cut oriented in the direction of a longitudinal axis of the stein component. In some embodiments, the annular groove may be at least partially filled with a fibrous, foam, or other biocompatible material.

In still other embodiments of the present invention, a stent-valve delivery system is provided. A first assembly is provided that includes an outer sheath and a guide wire tubing. The delivery system also includes a second assembly including a stent holder configured for removable attachment to at least one attachment element of a stent-valve. The stent-valve may be positioned over the guide wire tubing of the first assembly. The first assembly and the second assembly may be configured for relative movement with respect to one another in order to transition from a closed position to an open position. In the closed position, the outer sheath may encompass the stent-valve still attached to the stent holder and thus constrain expansion of the stent-valve. In the open position, the outer sheath may not constrain expansion of the stent-valve and thus the stent-Valve may detach from the stent holder and expand to a fully expanded configuration.

In some embodiments, the first assembly and the second assembly may be configured to transition from the closed position, to a partially-open position, to the open position. In the partially-open position, the stent-valve may expand partially but not detach from the steal holder because the outer sheath may still encompass the at least one attachment element of the stent-valve and the stent holder. When the stent-valve is in the partially-expanded configuration, it may be determined whether the stent-valve will be positioned correctly if the stent-valve is expanded to the fully expanded configuration. Alternatively or additionally, the functionality of the stent-valve may be tested (e.g., to determine whether the stent-valve will permit sufficient blood-flow) when the stent-valve is in the partially-expanded configuration.

In some embodiments, the first assembly of the stent-valve delivery system may include a coil-reinforced outer sheath and/or a substantially dome-shaped tip, which may provide resistance to kinking due to the bending moment acting onto the delivery system during positioning within, for example, an aortic arch.

In some embodiments, the stoat holder of the delivery system may include proximal and distal components positioned adjacent to one another (i.e., no gap). This may reduce or eliminate the risk of catching or damaging the outer sheath of the first assembly when closing the delivery device.

In some embodiments, the stent holder may include at least one chamfered edge positioned adjacent to at feast one attachment pin of the stent holder, where the at least one attachment pin is configured for removable attachment to an attachment element of a stent component. The chamfered edge may assist with the release and expansion of the stent-valve from the stent holder when the stent holder is rotated axially.

In still other embodiments of the present invention, an apparatus is provided for positioning and attaching a stent-valve comprising a plurality of attachment elements to a corresponding plurality of attachment pins of a stent holder. The apparatus may include an elongate, pliable member (e.g., suture or wire) configured to be threaded through the plurality of attachment elements. The apparatus may also include a tube for receiving the elongate, pliable member. Pulling the elongate, pliable member through the tubing while holding the tubing in a fixed position may collapse the stent-valve diameter to allow for engagement of the attachment elements to the attachment pins.

In some embodiments, an apparatus is provided for collapsing a diameter of a stent-valve to allow capture of the stent-valve within a sheath of a delivery system. The apparatus may include an elongate, substantially flat strip comprising a slit positioned perpendicular to a longitudinal axis of the strip. The elongate, substantially flat strip may include an end having a height less than a height of the slit, such that insertion of the end into the slit forms a loop. Upon placement of an expanded stent-valve within the loop, pulling the end through the slit causes a reduction of the loop diameter and thereby collapses the diameter of the stent-valve. The elongate, substantially flat strip may be formed from any suitable material including, for example, polymer and metal.

BRIEF DESCRIPTION OF THE DRAWINGS

For a better understanding of the present invention, reference is made to the following description, taken in conjunction with the accompanying drawings, in which like reference characters refer to like parts throughout, and in which.

DETAILED DESCRIPTION OF THE INVENTION

Figure 1:
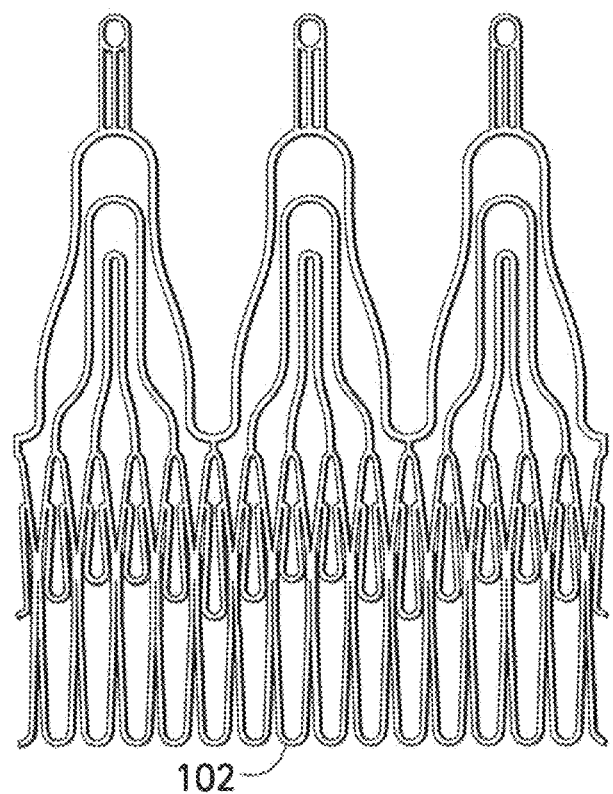
FIG. 1 shows a stent component that includes single struts in a proximal section of the stent according to some embodiments of the present invention.
Figure 2:
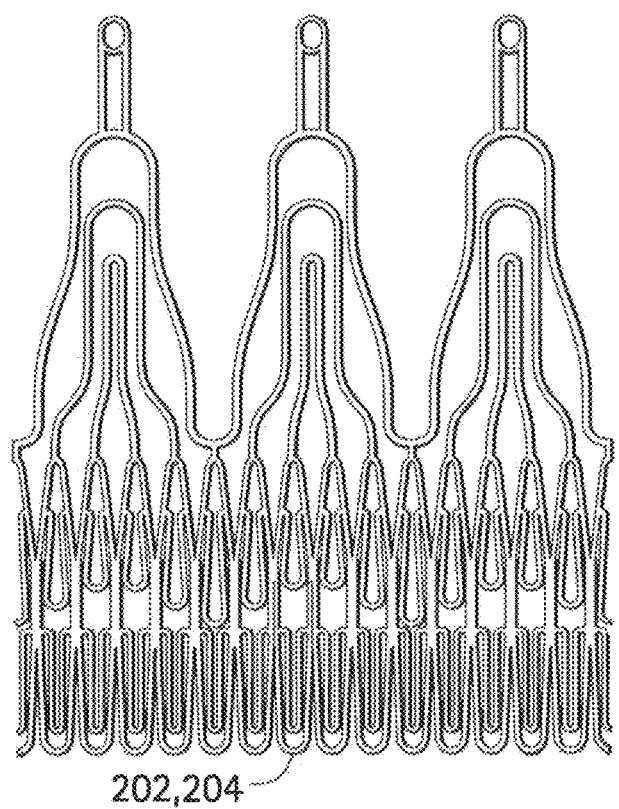
FIG. 2 shows a stent component that includes double struts in a proximal section of the stent according to some embodiments of the present invention.

FIG. 1 shows a stent component according to some embodiments that includes single struts 102 in a proximal section of the stent. FIG. 2 shows a stent component according to some embodiments that includes two struts (202, 204) in a proximal section of the stent. Such double struts may increase the radial resistance to crush of the stent (e.g., axial resistance) and the out of plane bending stiffness of the stent proximal section, thus improving the anchoring of the stent within, for example, a failed biological valve or a calcified native annulus. In FIG. 1, multiple (e.g., 10-15 or more) installations of single strut 102 may be provided, for example, side-by-side around the circumference of the scent. In FIG. 2, first strut 202 and second strut 204 are provided, where second strut 204 may be a reinforcement within first strut 202.

Figure 3:
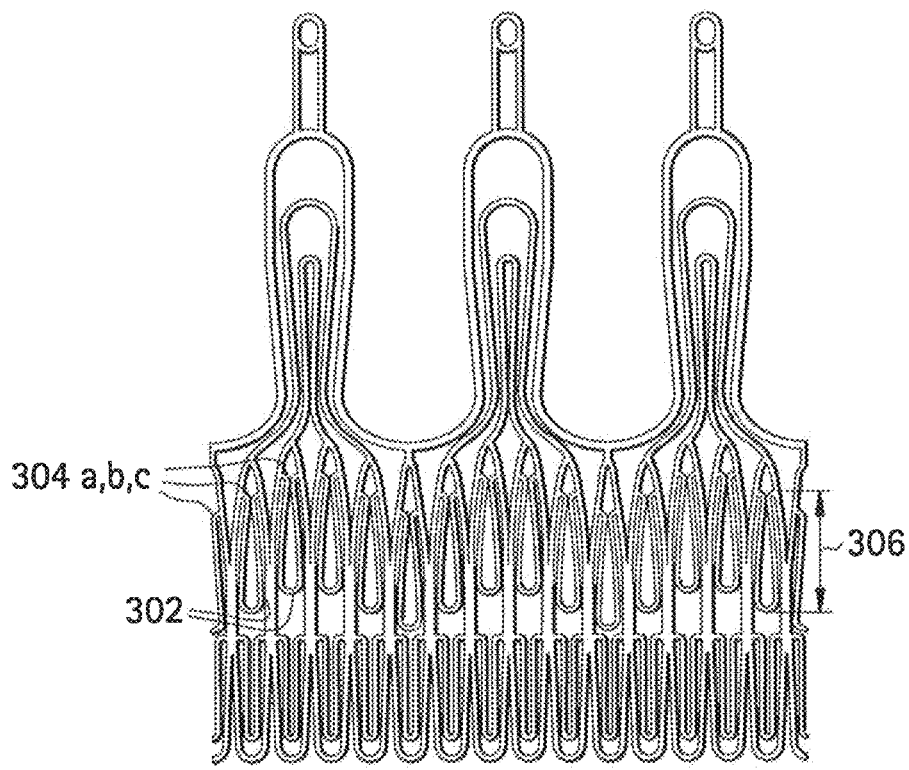
FIGS. 3 and 4 show stent components that include multiple locking elements positioned at multiple, different levels such that at least one locking element is located more proximally than another locking element according to some embodiments of the present invention.
Figure 4:
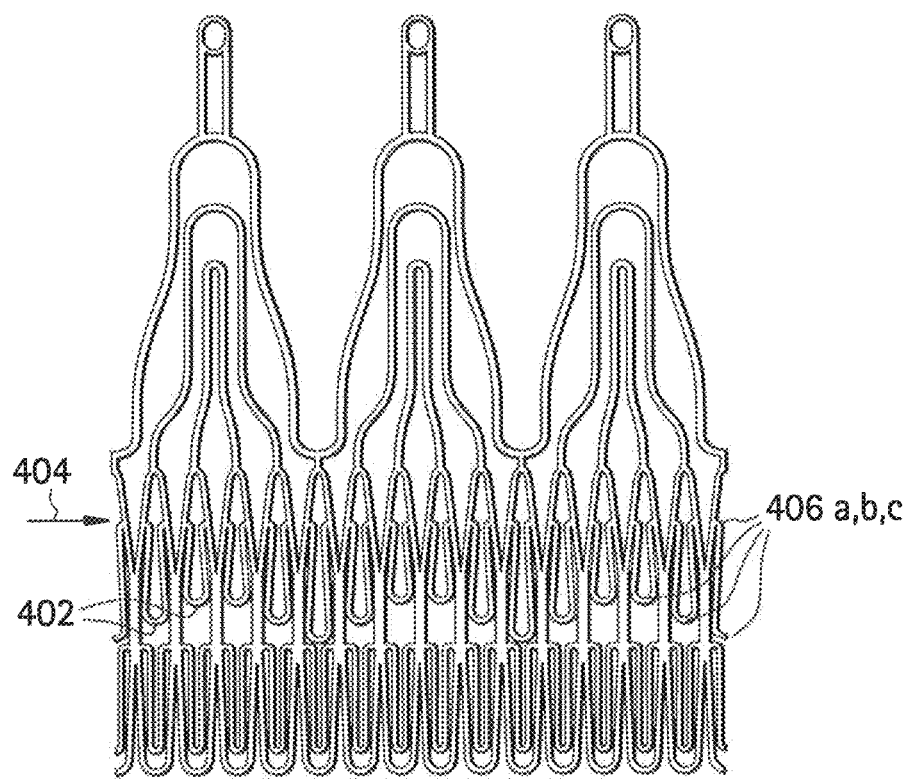

FIGS. 3 and 4 show some embodiments of stent components that include multiple locking elements positioned at multiple, different levels, such that at least one locking element is located more proximally than another locking element. The locking elements may engage, for example, a failed biological valve or calcified native annulus. En FIG. 3, the portions of locking elements 302 located adjacent to the outer surface of the stent component are positioned at multiple, different levels (304 a, b, c) and each locking element 302 has the same or similar length 306. These locking elements may have a similar out of plane bending stiffness. In FIG. 4, the portions of locking elements 402 located adjacent to the outer surface of the stent component are positioned at the same level 404 and the locking elements 402 have multiple different lengths (406 a, b, c). In the configuration of FIG. 4, the shorter locking elements 402 may have a higher out of plane stiffness. High out of plane bending stiffness may prevent a complete circular expansion of the stent-valve which could result in paravalvular leaks.

Figure 5:
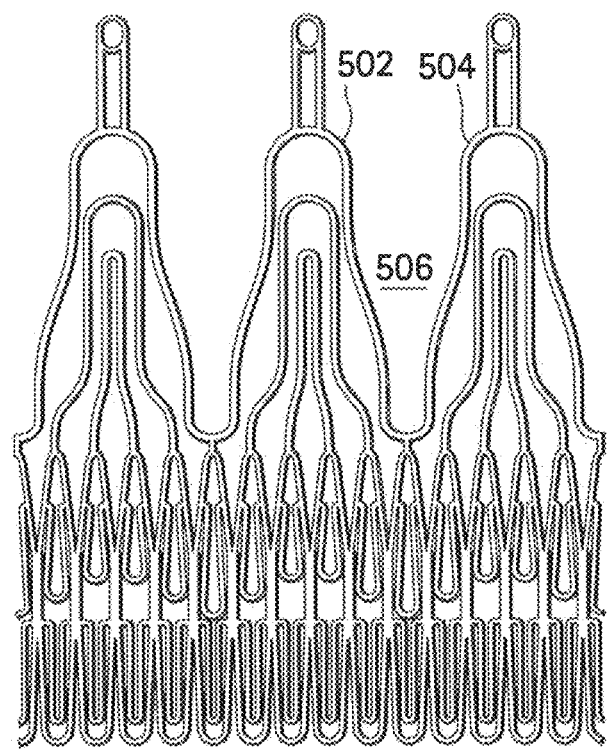
FIGS. 5 and 6 show stent components having, respectively, convex and concave stem configurations according to some embodiments of the present invention.
Figure 6:
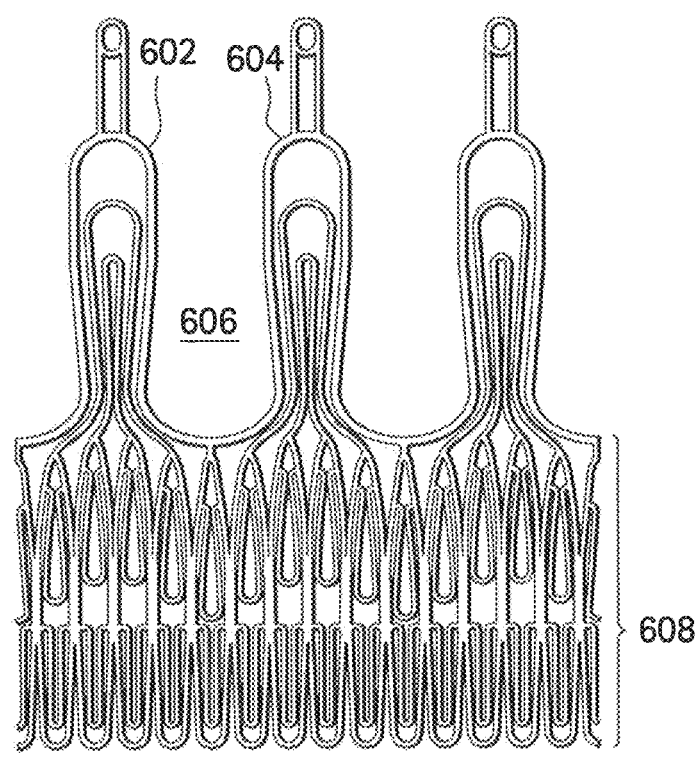

FIGS. 5 and 6 show stent components according to some embodiments having different stem (e.g., commissural post) configurations according to some embodiments of the present invention. As shown in FIG. 5, each of the external contours (e.g., wires) of adjacent stems 502 and 504 may have a generally convex shape 506. FIG. 6 shows another embodiment in which the external contours of adjacent stems (602, 604) collectively form a generally concave shape 606. In some embodiments, the concave shape may also have inward-sloping characteristic(s). For example, as shown in FIG. 6, each of the external arches slopes inwardly toward the center of the corresponding stem in the direction of the body 608 of the stent. The inclusion of a concavely-shaped stem may, for example, avoid the contact of the valve leaflets with the expanded stent during systole and improve the blood flow to the coronary arteries. Other embodiments of stent components include, for example, stents that include both convexly- and concavely-shaped stems (e.g., a stent component including at least one stem 502 and at least one stem 602).

Figure 7:
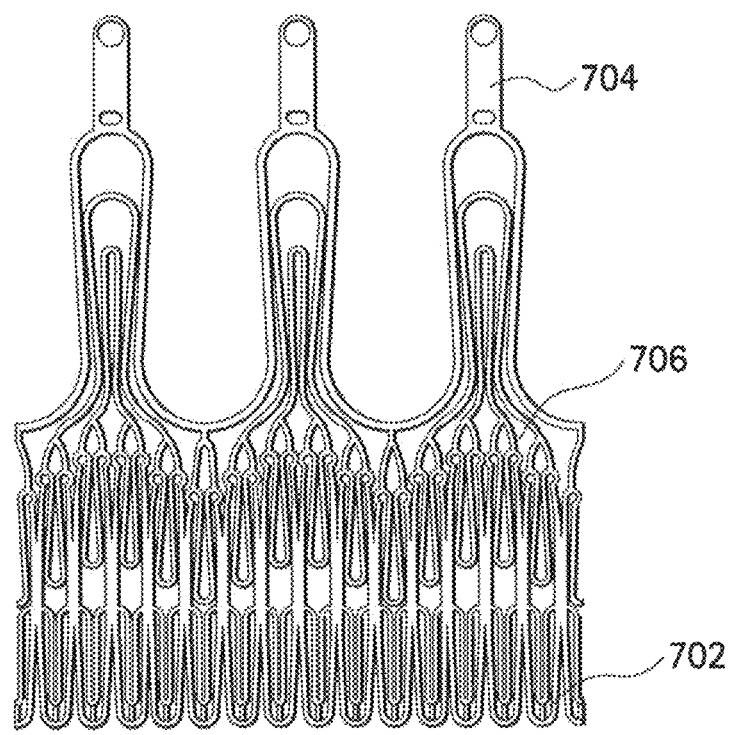
FIG. 7 shows a stent component that includes a reinforced proximal section and reinforced attachment elements according to some embodiments of the present invention.

FIG. 7 shows a stent component according to some embodiments that includes reinforcement of a proximal section of the stent with the connection of the double struts 702 (e.g., connection of struts 202 and 204 of FIG. 2). This increases the radial force/resistance to crushing of the stent and the out of plane bending stiffness of the elements forming the proximal section, thus improving the anchoring of the stent-valve within the calcified annulus. Furthermore, the attachment elements are reinforced 704 to reduce the risk of kinking under compression during stent-valve release. Geometry 706 has also been changed (e.g., optimized) to locally reduce stresses and strains.

Figure 8:
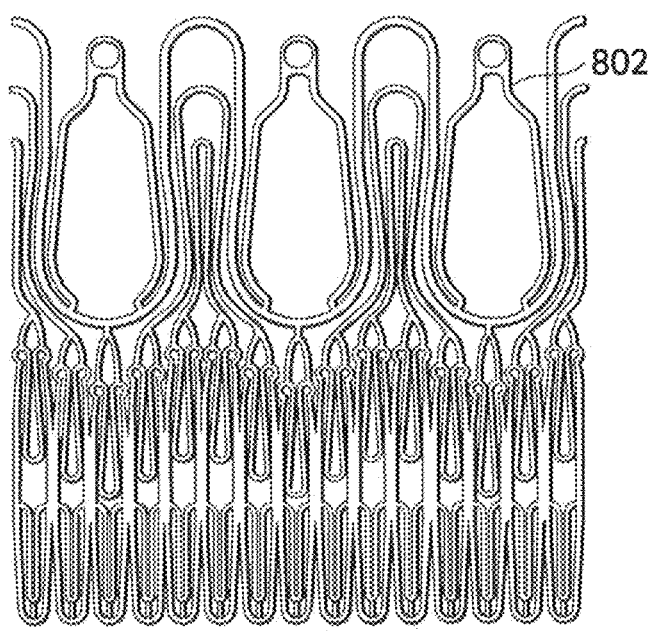
FIG. 8 shows a stent component that includes attachment elements positioned between commissural posts according to some embodiments of the present invention.

FIG. 8 shows a stent component according to some embodiments in which the attachment elements 802 are positioned between the commissural posts. This may reduce the overall stent length and accordingly the length of the delivery system, thus avoiding its distal section entering deeply into the ascending aorta/aortic arch during stent-valve release.

Figure 9:
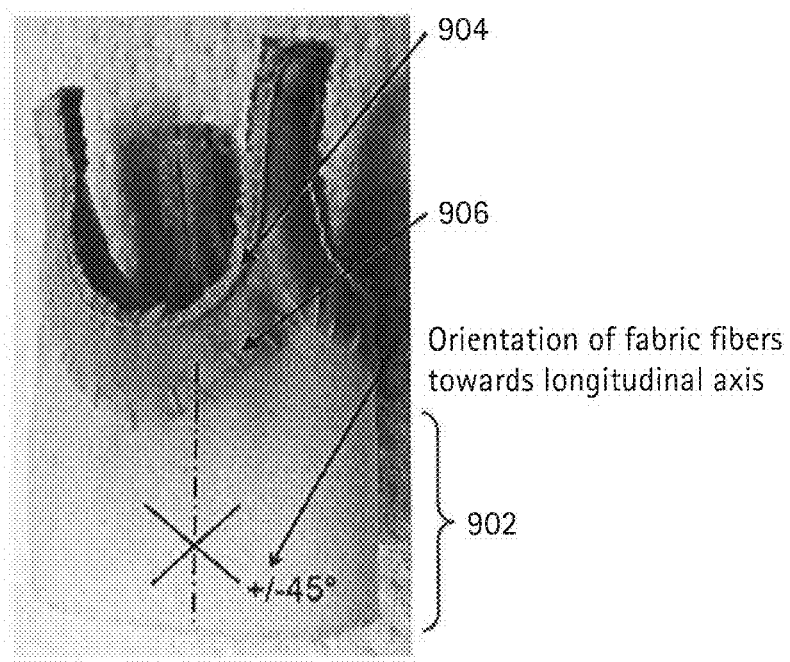
FIG. 9 shows a fabric reinforcement for a valve component that covers all, or substantially all, of the valve outer surface and forms a skirt according to some embodiments of the present invention.
Figure 10:
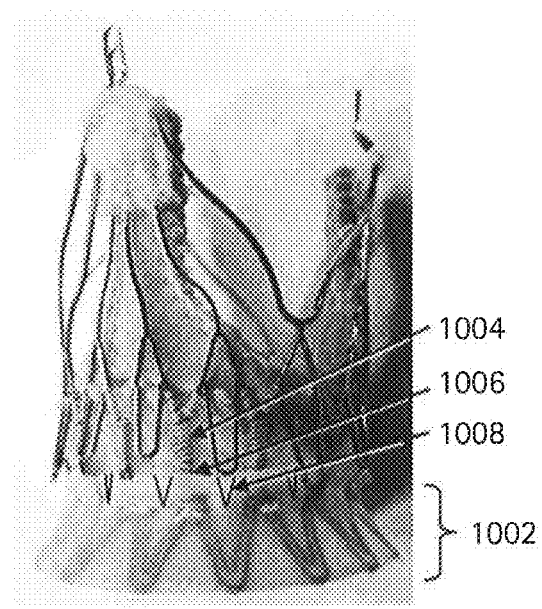
FIG. 10 shows details regarding the suturing the valve component and fabric of FIG. 9 to a stent according to some embodiments of the present invention.

FIGS. 9 and 10 show additional details regarding stent-valves in accordance with some embodiments of the present invention. In FIG. 9, a fabric reinforcement is provided that covers all, or substantially all, of the valve outer surface down to the skirt 902. This may prevent pulling out of sutures and wearing of the valve due to contact with the stein. A continuous suture 904 along the trimmed aortic sinus may be provided, which may allow for firm fixation of the valve to the stent commissural posts. Together with continuous suture 906 along the perimeter of the inflow margin, suture 904 may also increase seal integrity. The fabric that covers the skirt may be integral to and continuous with the fabric that extends between sutures 904 and 906, although in other embodiments the skirt fabric and the fabric between sutures 904 and 906 may be two separate pieces of fabric that are joined by the sutures. In some embodiments, the fibers of the fabric may be oriented +/−45° with respect to the stent-valve longitudinal axis. This may allow the diameter of the skirt to self adapt to the diameter of the stent in its proximal grooved/flared section by slightly re-orienting the fiber direction (smaller angle within groove, larger angle within flared section).

FIG. 10 shows details regarding the suturing the valve and fabric of FIG. 9 to a stent according to some embodiments of the present invention. As shown, the proximal section of the skirt 1002 may be folded over the proximal flared/grooved proximal stent section. Y-shaped sutures 1004 may be provided that hold the valve firmly within the stent and increase seal integrity. In some embodiments, each Y-shaped connection may be made out of one or more independent sutures, where multiple sutures may be provided to avoid leakage in case of a rupture of any single stitch. Free floating edge 1006 of the skirt may be positioned within the groove of the stent and may serve as a further blood barrier by promoting clotting. In some embodiments, longitudinal cuts 1008 may be made along the free floating edge between the sutures to build flexible flaps around the circumference of the stent within the groove. This may improve the barrier effect and increase conformability of the skirt. Alternatively or additionally, the sealing of the prosthesis may be improved by at least partially filling the groove with a fibrous, foam like, or other suitable biocompatible material. The skirt may have a smooth inner surface to minimize blood shear at the annular inflow tract of the prosthesis. A more structured surface may be provided on the outer surface of the prosthesis in order to, for example, improve the sealing of the stent-valve at the implantation site.

Figure 11:
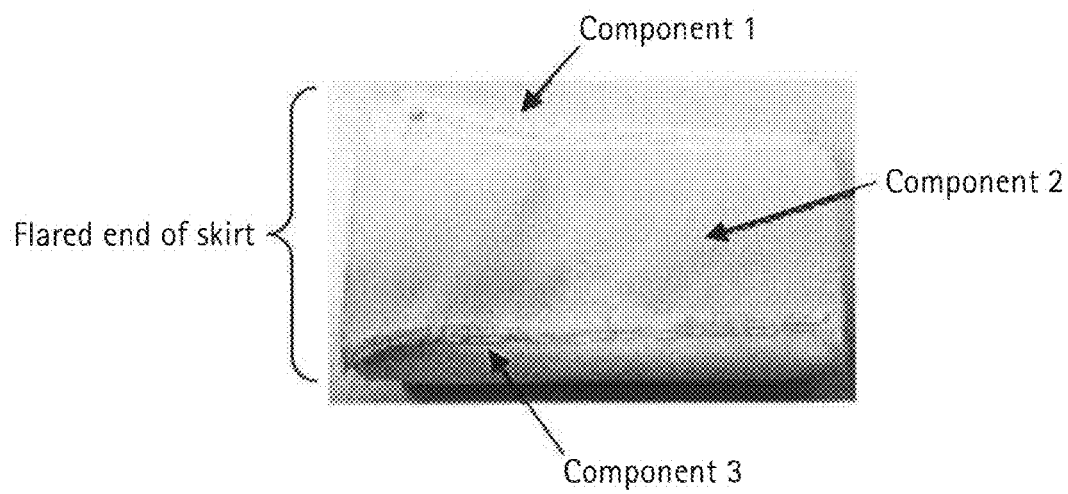
FIG. 11 shows a stent-valve that includes a multi- (e.g., three) component fabric reinforcement according to some embodiments of the present invention.

FIG. 11 shows a stent-valve according to some embodiments that includes a multi- (e.g., three) component fabric reinforcement. Each component may have a trapezoid geometry to accommodate the variation of the stent inner diameter over its longitudinal axis. When the components are sutured together, they may form a cylindrical or part-cylindrical skirt, which is flared at one extremity to avoid constraining the stent and thereby reducing its anchoring force within the annulus.

Figure 12:
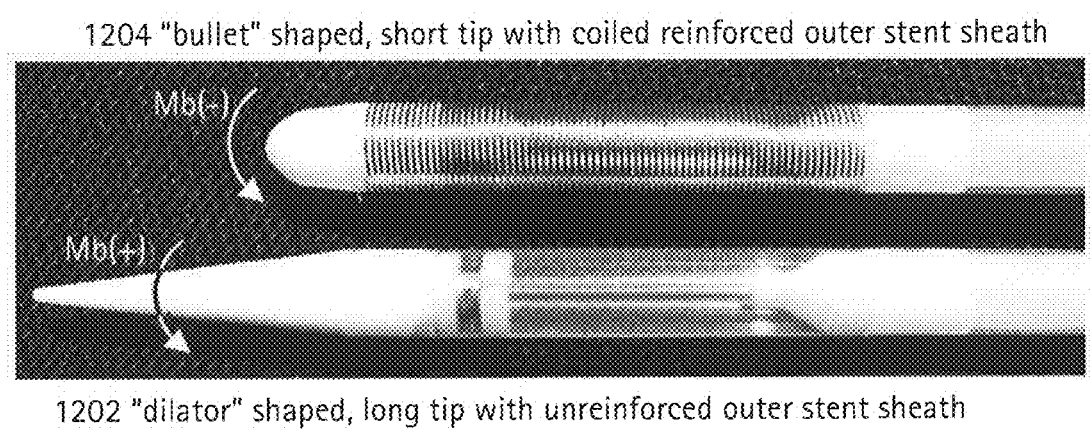
FIG. 12 shows two configurations for the distal section of a stent-valve delivery system according to some embodiments of the present invention.

FIG. 12 shows two configurations for a distal section of a stent-valve delivery system in accordance with some embodiments of the present invention. Distal configuration 1202 includes a generally dilator shaped, longer tip with an unreinforced outer stent sheath. In contrast, distal configuration 1204 includes a generally bullet or domed shaped, shorter tip with a coil-reinforced outer stent sheath. Several manufacturing technologies are available for manufacturing such coil-reinforced sheaths including, for example, extrusion of an inner and an outer tubing, coiling of a stainless steel wire, and assembling the three components by fusion bonding on a mandrel. Relative to distal configuration 1202, distal configuration 1204 may have improved resistance to kinking due to the bending moment acting onto the delivery system during positioning within, for example, an aortic arch. More specifically, the coil-reinforced stent outer sheath may increase the mechanical kink resistance of the stent delivery system. The use of the bullet shaped tip with reduced length may decrease the bending moment of the delivery system.

Figure 13:
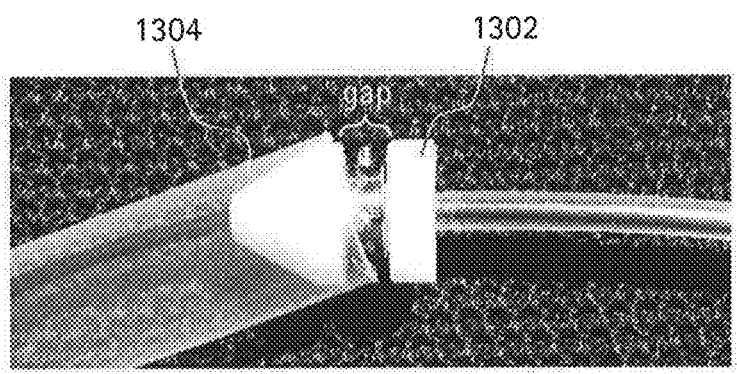
FIGS. 13 and 14 show two configurations of a stent holder of stent-valve delivery system according to some embodiments of the present invention.
Figure 14:
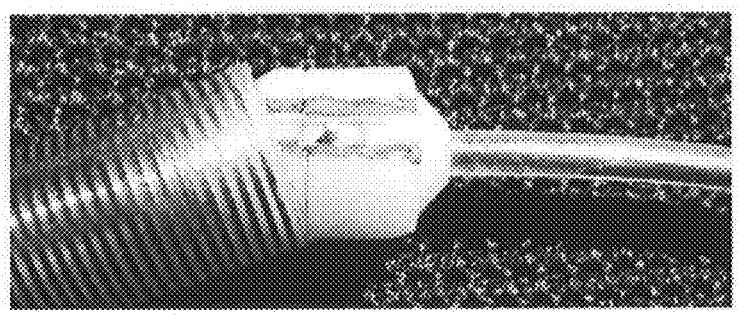

FIGS. 13 and 14 show two configurations of a stent holder of stent-valve delivery system in accordance with some embodiments of the present invention. In FIG. 13, the stent holder includes proximal and distal components separated by a gap 1302. En some embodiments, the component actually holding the stent is the middle, metallic component. The distal component may be conically shaped to facilitate closing of the sheath and to avoid catching the pins. The proximal component may serve as a guide for the attachment elements of the stent and may prevent them from kinking under compression during stent-valve release. In some embodiments, the distal, metallic, and proximal components may be separate pieces, whereas in other embodiments they may be a single piece of solid construction. In FIG. 14, the proximal and distal components are positioned adjacent to one another and thus the gap is removed, which may reduce or eliminate the risk of catching or damaging the stent outer sheath 1304 when closing the delivery device.

Figure 15:
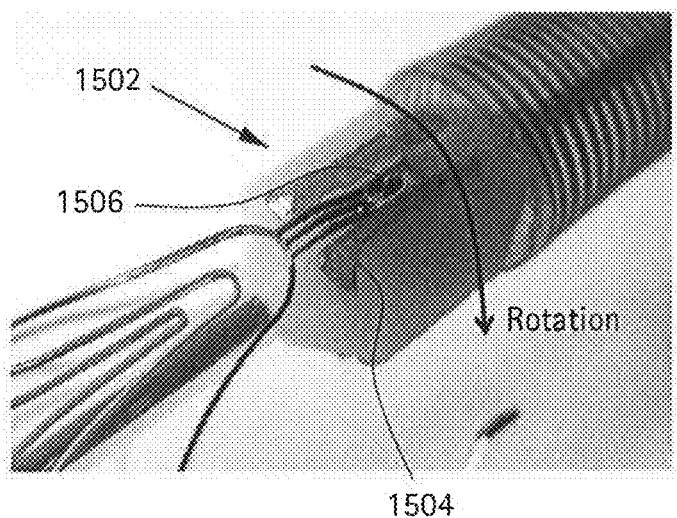
FIG. 15 shows a stent holder with at least one chamfered edge according to some embodiments or the present invention.

FIG. 15 shows another configuration of a stent holder in accordance with some embodiments of the present invention. As shown, one or both of the edges (1502, 1504) located adjacent to element 1506 (e.g., pin) configured for removable attachment to a stent component may be chamfered. In some embodiments, the stent holder may include multiple (e.g., three) such elements 1506 and adjacent chamfered edge(s). The inclusion of chamfered edge(s) on the surface of the stent holder may help to release the stent-valve from element(s) 1506 of the stent holder when a rotational force is applied, for example, to a hold handle of the delivery system.

Figure 16A:
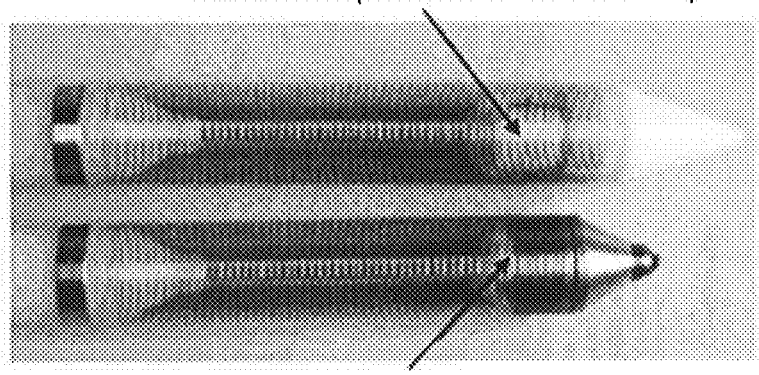
FIG. 16 shows a stent-valve delivery system in which a distal section of the delivery system has a reduced length according to some embodiments of the present invention.
Figure 16B:
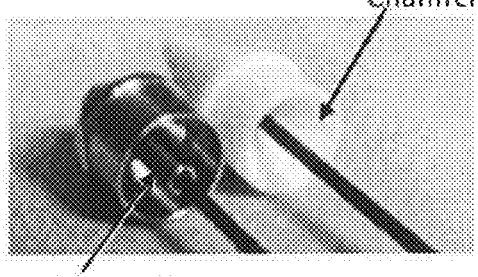
Figure 17A:
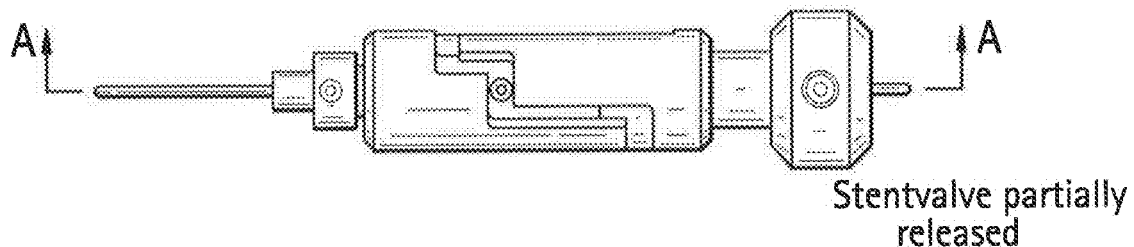
FIG. 17 shows a stent-valve delivery system with gearbox type release handle according to some embodiments of the present invention.
Figure 17B:
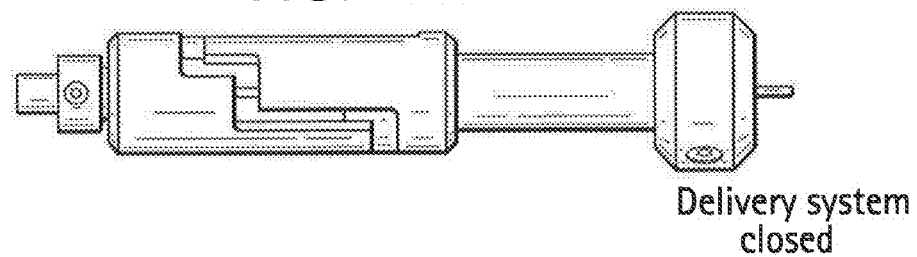
Figure 17C:
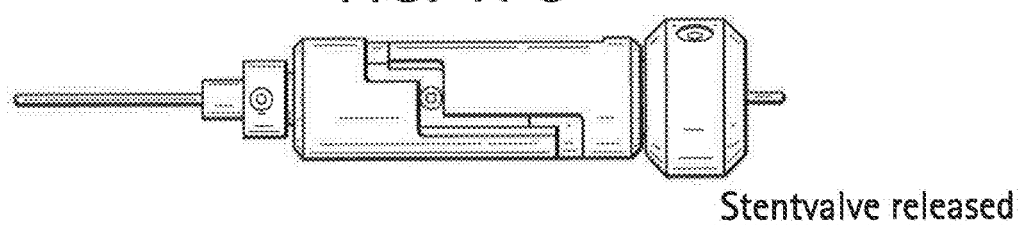
Figure 17D:
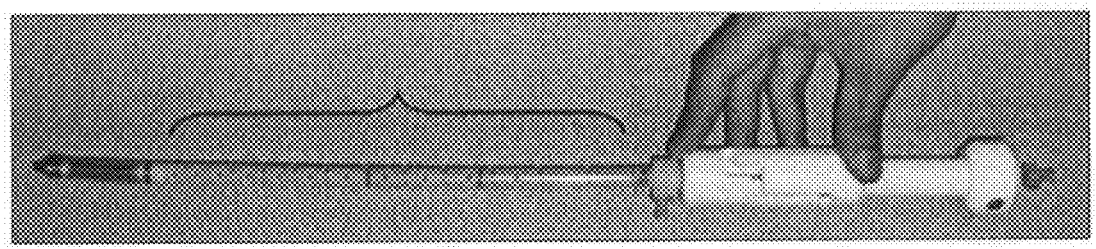

FIG. 16 shows a stent-valve delivery system in which a distal section of the delivery system has a reduced length (e.g., the length which enters into the ascending aorta) relative to a delivery system with a chamfered distal tip. A hollow tip 1602 may be provided that encapsulates the attachment elements/stentholder assembly, which may provide for the reduced length. Placing the attachment elements between the commissural posts may allow for a further reduction in the length of the delivery system.

FIG. 17 shows a stent-valve delivery system with gearbox type release handle according to some embodiments, which includes opened and closed positions. To move from one position to the other, a rotation of the handle is required prior to translation, thus reducing handling errors.

Figure 18:
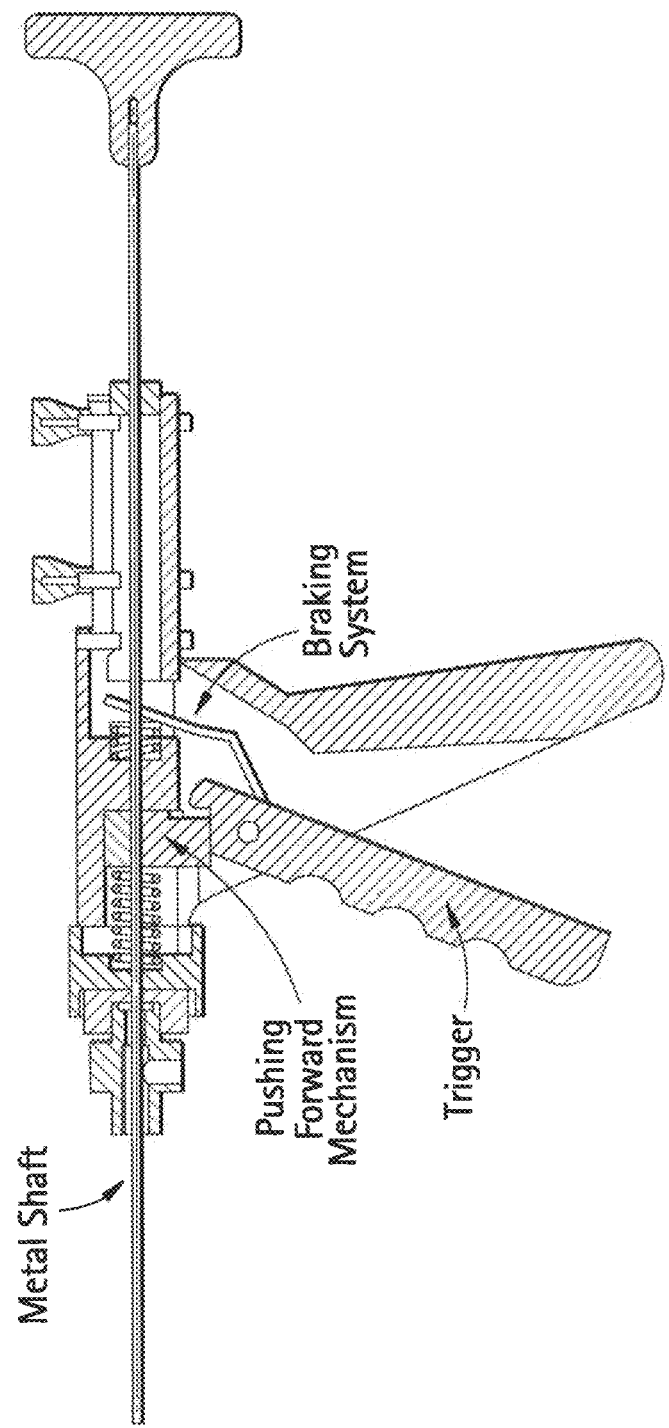
FIG. 18 shows a stent-valve delivery system with a trigger type release handle according to some embodiments of the present invention.

FIG. 18 shows a stent-valve delivery system with a trigger type release handle according to some embodiments. In such embodiments, translational movement for opening the delivery system and releasing the stent-valve may be provided by pressing the trigger, thus releasing a braking system and pushing forward the metal shaft connected to the stent cuter sheath. This system advantageously allows a one hand release of the stent-valve, whereas the other hand takes care of the positioning of the implant. The design of this release handle may be similar to, for example, products commercially available for dispensing, for example, silicone.

Figure 19:
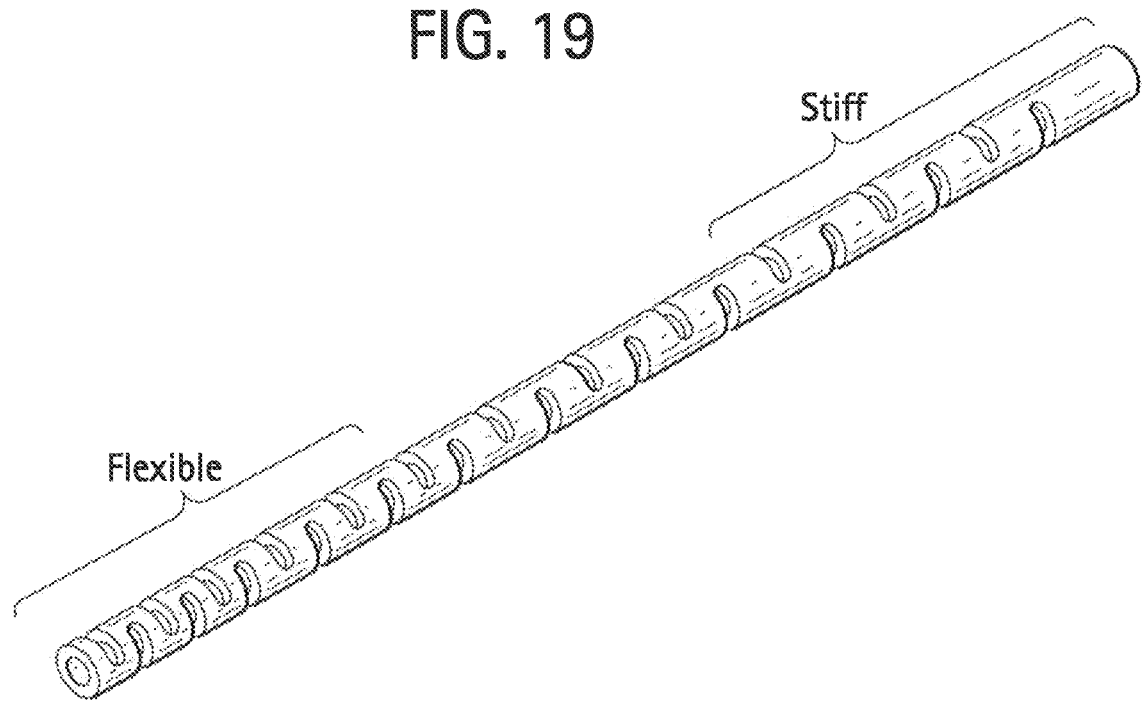
FIG. 19 shows a shaft of a stent-valve delivery system that has a bending stiffness which varies from its proximal to distal ends according to some embodiments of the present invention.

FIG. 19 shows a mid section of a stent-valve delivery system according to some embodiments, which may include a shaft having a bending stiffness which varies from its proximal to distal ends. A stiff proximal shaft may provide for pushability of the delivery system, whereas the flexible distal section may allow for an improved trackability in curves. The shaft may include openings (e.g., water jet cut openings) along its longitudinal axis (FIGS. 17 and 19), where the openings may be oriented towards two perpendicular axes with respect to the shaft cross section.

Figure 20:
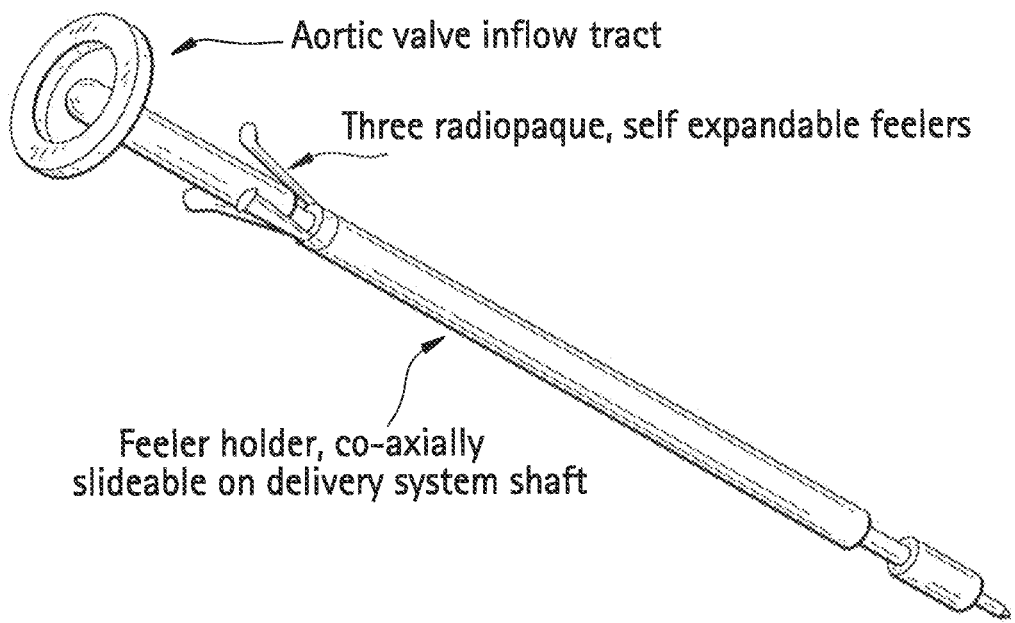
FIG. 20 shows a positioning device for assisting a physician to implant a stent-valve at an appropriate location according to some embodiments of the present invention.
Figure 20:
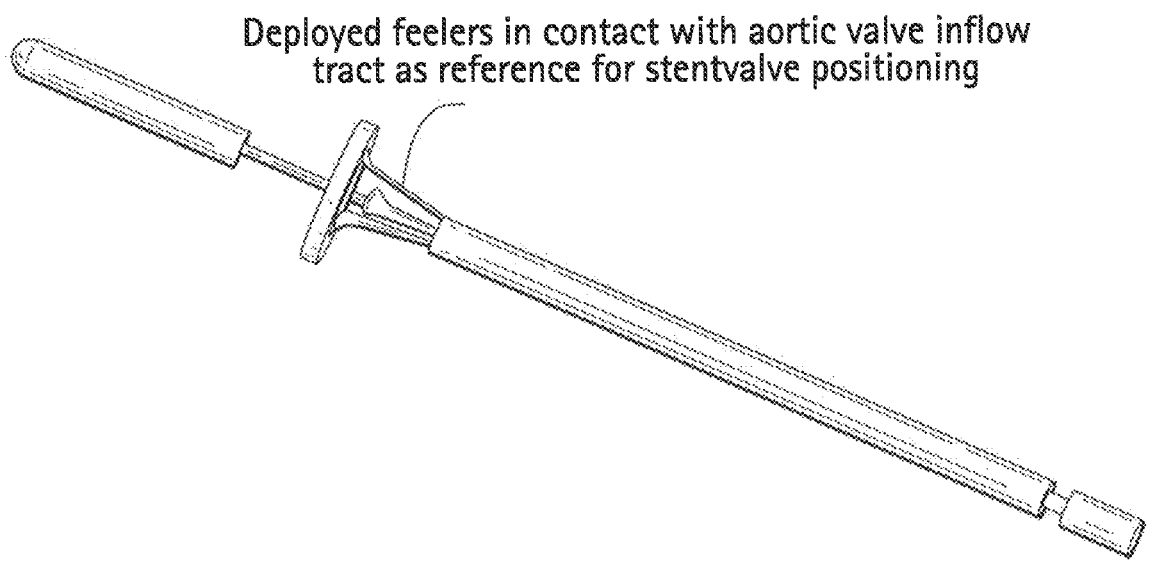

FIG. 20 shows a positioning device for assisting a physician to implant a stent-valve at an appropriate location according to some embodiments. The positioning device comprises three self expanding (e.g. nitinol) fingers or feelers constrained within an outer sheath, which may be co-axially slideable into the stent-valve delivery system. By retracting the outer sheath, the feelers start to expand and can be positioned under the inflow tract of, for example, the aortic valve under fluoroscopic assistance. By exerting a slight force towards the annulus, the three fingers may act as a landmark for implanting the stent-valve.

Figure 21A:
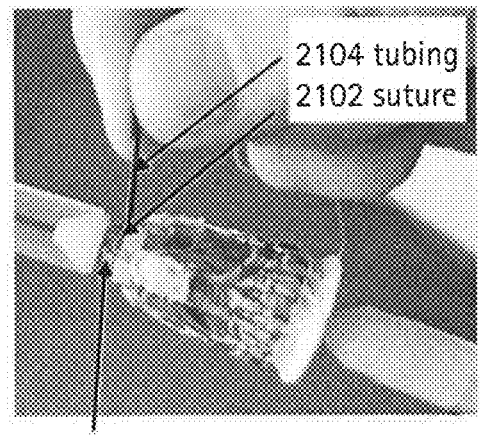
FIGS. 21A-C show a system and corresponding method for positioning and attaching a stent-valve to a stent holder of a delivery system according to some embodiments of the present invention.
Figure 21B:
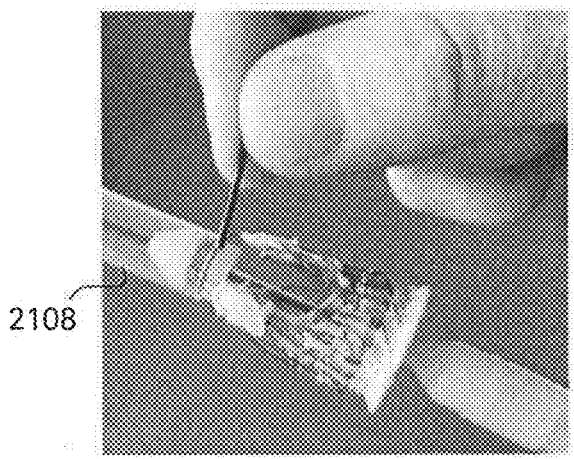
Figure 21C:
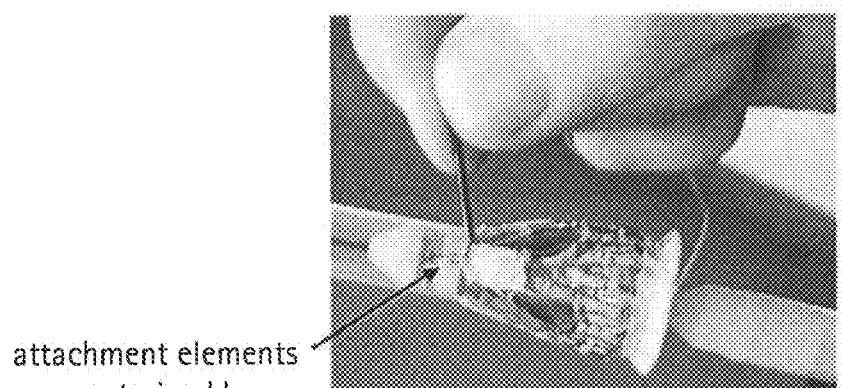

FIGS. 21A-C show a system and corresponding method for positioning and attaching a stent-valve to stent holder in accordance with some embodiments of the present invention. As shown in FIG. 21A, a suture or other pliable, continuous element 2102 (e.g., wire) may be threaded through the attachment elements of the stent component and then through a cannula or tubing 2104. By pulling the suture and holding the tubing, the stent-valve diameter may be collapsed and the attachment elements may engage the element(s) (e.g., pins 2106) of the stent holder. In some embodiment, both ends of the suture are free (such that both ends are fed through the tube and then pulled). In other embodiments, one end of the suture is free whereas the other end is fixed (e.g., to the tubing), such that only one end of the suture is thread through the tubing and pulled. Subsequently, outer sheath 2108 may be pulled proximally over the attachment elements, as shown in FIGS. 21B and 21C. The suture may then be removed by pulling it back through the attachment elements.

Figure 22A:
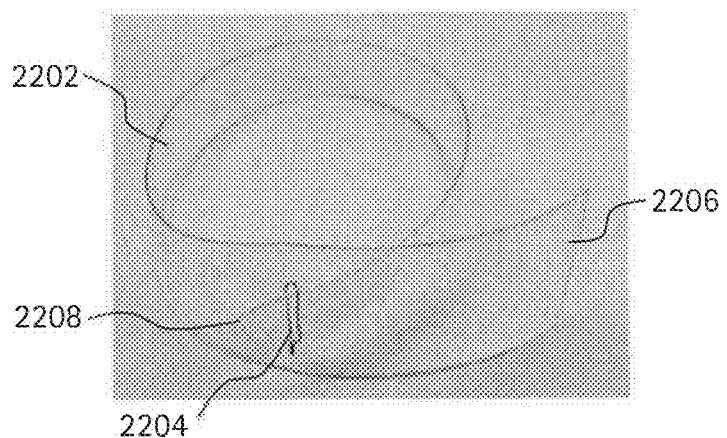
FIGS. 22A-C show a system and corresponding method for crimping a stent-valve onto a delivery system according to some embodiments of the present invention.
Figure 22B:
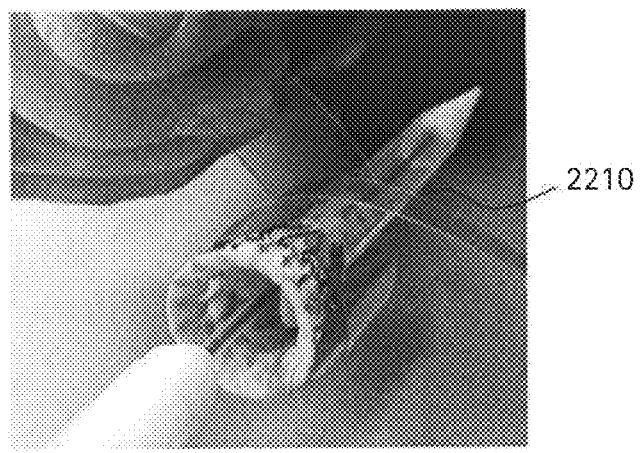
Figure 22C:
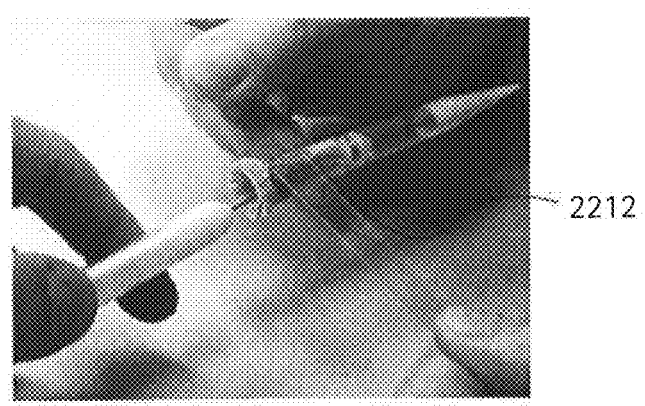

FIGS. 22A-C show a system and corresponding method for crimping a stent-valve onto a delivery system according to some embodiments. FIG. 22A shows a thin, flat (e.g., polymer or metallic) strip 2202 with a slit 2204 perpendicular to its longitudinal axis and having a wide edge 2206 at one end and a narrower edge 2208 at the opposite end. When the narrow edge is inserted into the slit (i.e., the slit having a greater height than a height of the narrow edge), the strip forms a loop. As shown in FIGS. 22B and 22C, when a stent-valve is placed within the loop, pulling on the edges at the two extremities of the strip causes a reduction of the loop diameter 2210 thereby crimping the stent-valve. The crimped stent-valve can then be stepwise constrained by the outer sheath 2212. Generally, the positioning and crimping systems shown in FIGS. 21A-C and 22A-C provide for ease of use by physicians or other technicians. In some embodiments, these positioning and crimping systems may be low cost and disposable, and may be delivered as sterile accessories together with the delivery system and/or the stent-valve.

Thus it is seen that stent-valves (e.g., single-stent-valves, double-stent-valves) and associated methods and systems for surgery are provided. Although particular embodiments have been disclosed herein in detail, this has been done by way of example for purposes of example and illustration only, and is not intended to be limiting with respect to the scope of the appended claims, which follow. To that end, any reference to measurements, distances and the like, are for illustrative/example purposes. In particular, it is contemplated by the applicant that various substitutions, alterations, and modifications may be made without departing from the spirit and scope of the invention as defined by the claims. Other aspects, advantages, and modifications are considered to be within the scope of the following claims. The claims presented are representative of some of the inventions disclosed herein. Other, unclaimed inventions are also contemplated. The applicant reserves the right to pursue such inventions in later claims.

What is claimed is:

1. A replacement valve for use within a human body comprising:
   a valve component comprising an outer surface covered at least partially with a fabric skirt configured to extend below the valve component; and
   a stent component for housing the valve component,
   wherein the stent component and valve components are configurable into at least a collapsed configuration for percutaneous delivery and an expanded configuration after implantation, a free edge of the fabric skirt wraps a bottom portion of the stent component and is affixed to the stent component via a plurality of sutures; and
   at least a portion of the fibers of the fabric skirt are oriented at substantially 45 degrees with respect to a longitudinal axis of the valve component in the expanded configuration.

2. The replacement valve of claim 1, wherein the free edge of the skirt comprises at least one cut oriented in a direction of a longitudinal axis of the stent component.

3. The replacement valve of claim 2, wherein a plurality of cuts are made along the free edge between sutures of the plurality of sutures of the free edge to the stent component.

4. The replacement valve of claim 3, wherein the free edge includes a plurality of flexible flaps around a circumference of the stent component.

5. The replacement valve of claim 4, wherein the plurality of flexible flaps is configured to at least one of promote blood clotting to establish a blood barrier and assist the skirt in conforming to the stent component.

6. The replacement valve of claim 1, wherein the bottom portion of the stent component has an undulating lower edge, and wherein the free edge of the skirt that wraps the bottom portion is affixed to the stent component at one or more locations above the undulating lower edge.

7. The replacement valve of claim 6, wherein the bottom portion of the stent component is defined by multiple installations of a strut having an apex, wherein there are at least ten installations.

8. The replacement valve of claim 1, wherein the skirt comprises first and second separate pieces of fabric joined by a plurality of sutures.

9. A replacement valve for use within a human body comprising:
   a valve component comprising an outer surface covered at least partially with a fabric skirt configured to extend below the valve component; and
   a stent component for housing the valve component,
   wherein the stent component and the valve component are configurable into at least a collapsed configuration for percutaneous delivery and an expanded configuration after implantation, a free edge of the fabric skirt wraps a bottom portion of the stent component and affixed to the stent component via a plurality of sutures; and
   at least a portion the fabric skirt includes fibers which are oriented substantially plus 45 degrees with respect to a longitudinal axis of the valve component and fibers which are oriented substantially minus 45 degrees with respect to a longitudinal axis of the valve component in the expanded configuration.

10. The replacement valve of claim 9, wherein the free edge of the fabric skirt comprises at least one cut oriented in a direction of a longitudinal axis of the stent component.

11. The replacement valve of claim 10, wherein a plurality of cuts are made along the free edge between sutures of the plurality of sutures of the free edge to the stent component.

12. The replacement valve of claim 11, wherein the free edge includes a plurality of flexible flaps around a circumference of the stent component.

13. The replacement valve of claim 12, wherein the plurality of flexible flaps are configured to promote at least one of blood clotting to establish a blood barrier and to assist the fabric skirt in conforming to the stent component.

14. The replacement valve of claim 10, wherein the bottom portion of the stent component has an undulating lower edge, and wherein the free edge of the fabric skirt wraps the bottom portion and is affixed to the stent component at one or more locations above the undulating lower edge.

15. The replacement valve of claim 14, wherein the bottom portion of the stent component is defined by multiple installations of a first strut having an apex and a second strut located within the first strut, wherein the end of the second struts connected to the end of the first strut, which multiple installations include at least ten installations.

16. The replacement valve of claim 9, wherein the fabric skirt comprises a first separate piece of fabric and a second separate piece of fabric joined by a plurality of sutures.

17. The replacement valve of claim 9, further comprising a strip having a first portion having a first width and a second portion having a second width extending longitudinally from the first portion, wherein the first portion having a first width includes a slit transverse to a longitudinal direction of the strip, the slit having transverse extents within the first portion which are less than the first width and greater than the second width.

18. A replacement valve for use within a human body comprising:
 a valve component comprising an outer surface covered at least partially with a fabric reinforcement;
 a stent component housing the valve component therein; and
 a fabric skirt;
 wherein the stent component and valve components are configurable into at least a collapsed configuration for percutaneous delivery and an expanded configuration after implantation;
 wherein at least a portion of the fabric skirt is disposed on an outer surface of the stent component and affixed to the stent component via at least one suture; and
 wherein at least a portion of the fibers of the fabric reinforcement are oriented at substantially 45 degrees with respect to a longitudinal axis of the valve component in the expanded configuration.

19. The replacement valve of claim 18, wherein the fabric reinforcement is affixed to the stent component via at least one suture.

20. The replacement valve of claim 18, wherein the fabric skirt is directly connected to the fabric reinforcement.

* * * * *